United States Patent
Alexander et al.

(10) Patent No.: US 6,358,996 B1
(45) Date of Patent: Mar. 19, 2002

(54) STABLE ISOTOPE LABELING OF PACLITAXEL

(75) Inventors: Michael S. Alexander, McMinnville, OR (US); James D. McChesney, Boulder; Jan Zygmunt, Longmont, both of CO (US)

(73) Assignee: NaPro BioTherapeutics, Inc., Boulder, CO (US)

( * ) Notice: Subject to any disclaimer, the term of this patent is extended or adjusted under 35 U.S.C. 154(b) by 0 days.

(21) Appl. No.: 09/591,159

(22) Filed: Jun. 9, 2000

(51) Int. Cl.$^7$ ............................................... A61K 31/335
(52) U.S. Cl. ........................ 514/449; 549/510; 549/511
(58) Field of Search ................................. 549/510, 511; 514/449

(56) References Cited

U.S. PATENT DOCUMENTS

| | | | |
|---|---|---|---|
| 5,675,025 A | 10/1997 | Sisti et al. | |
| 5,684,175 A | 11/1997 | Sisti et al. | |
| 5,688,977 A | 11/1997 | Sisti et al. | |
| 5,750,736 A | 5/1998 | Sisti | |
| 5,750,737 A | 5/1998 | Sisti et al. | |
| 5,770,745 A | 6/1998 | Swindell et al. | |
| 5,914,411 A | 6/1999 | Sisti et al. | |
| 5,939,566 A | 8/1999 | Swindell et al. | |
| 5,948,919 A | 9/1999 | Sisti et al. | |
| 5,973,170 A | 10/1999 | Sisti et al. | |
| 6,048,990 A | 4/2000 | Liang et al. | |
| 6,066,749 A | 5/2000 | Sisti et al. | |
| 6,072,060 A | 6/2000 | Swindell et al. | |
| 6,107,497 A | 8/2000 | Sisti et al. | |

*Primary Examiner*—Amelia Owens
(74) *Attorney, Agent, or Firm*—Mark H. Weygandt; Timothy J. Martin; Michael R. Henson (57) ABSTRACT

A chemical compound comprising an isotopically labeled analog of a standard taxane molecule, wherein said isotopically labeled analog is synthetically formed to have incorporated therein at a selected position a stable isotope of an element existing at said selected positon in said standard taxane molecule, said isotope having amass different form a mass of a mass of a most abundantly occurring isotope of said element in nature, such that said isotopically labeled analog has a molecular weight different form a molecular weight of said standard taxane molecule.

35 Claims, 3 Drawing Sheets

STABLE ISOTOPE LABELING OF PACLITAXEL

FIELD OF THE INVENTION

The present invention is directed to the synthesis and composition of isotopically labeled paclitaxel and related taxane compounds. The present invention is more particularly directed to paclitaxel and related taxane molecules having stable isotopes synthetically incorporated therein at common positions in the chemical structure thereof. The present invention is more specifically directed to a carbon-13 labeled paclitaxel useful as an internal standard for HPLC/MS analysis of biological tissues for quantitation of taxanes. More particularly, the present invention is directed to synthesis and composition of carbon-13 labeled paclitaxel for use as an internal standard for the HPLC/MS analysis of biological tissue samples of clinical and toxicology pharmacokinetic and pharmacodynamic studies.

BACKGROUND OF THE INVENTION

Various taxane compounds are known to exhibit anti-tumor activity. As a result of this activity, taxanes have received increasing attention in the scientific and medical community. Primary among these is a compound known as "paclitaxel", which is also referred to in the literature as "taxol". Paclitaxel has been approved for the chemotherapeutic treatment of several different varieties of tumors, and the clinical trials indicate that paclitaxel promises a broad range of potent anti-leukemic and tumor-inhibiting activity. Paclitaxel has the formula:

Paclitaxel is a microtubule poison characteristic of a new class of anticancer drugs. In contrast to other natural spindle poisons, such as vinca alkaloids, taxol increases both the assembly and stability of cellular microtubules, and blocks the cell cycle in late G2 and M phases. It has shown significant activity in clinical trials against a number of human tumors, including breast, lung, head, neck, and ovarian carcinomas. Several pharmacokinetic studies, based on high-performance liquid chromatography (HPLC) and ultraviolet (UV) detection, have been reported. In most of these early investigations, the disappearance of taxol from plasma was found to follow a bi-exponential elimination model. In clinical pharmacological studies, several investigators have demonstrated that total urinary excretion of unmetabolized taxol ranges from 1.5% to 9% with a substantial inter-patient variability. These data suggest that renal clearance contributes little to systemic clearance. Conversely, metabolism, biliary excretion and/or extensive tissue binding probably account for the bulk of taxol disposition. Cytochrome P450 enzymes involved in the biotransformation of taxol have been identified using human liver microsomes and various over-expressed human cytochrome P450 isozymes. Preliminary studies showed that 6-hydroxytaxol, the major metabolite of taxol in human bile, was also present in plasma. Other putative minor metabolites were also detected in the plasma of human patients. Despite these promising observations, the low concentration of taxol derivatives presents a major difficulty for analysis of paclitaxel and its derivatives and metabolites in biological samples.

Mass spectrometry is a powerful technique for taxoid identification. Electron impact (EI), chemical ionization (CI), desorption chemical ionization (DCI), fast atom bombardment (FAB), electrospray (ES) ionization and matrix-assisted laser desorption/ionization (MALDI) techniques have all been used for the mass spectrometric analysis of taxol, taxol-related diterpenoids, and taxol metabolites. Characterization and quantification of taxanes by tandem mass spectrometry (MS/MS) has also been described. All of these mass spectrometry procedures require the separation of the various taxane derivatives from biological fluids. This purification is labor-intensive and requires large volumes of fluids, due to the low concentration of these compounds in human plasma, urine and bile. The direct combination of mass spectrometry with chromatographic techniques offers a new and effective alternative for metabolic studies which involve the analysis of complex biological samples, such as cell culture medium, plasma, bile and urine. HPLC has been successfully interfaced with thermospray (TSP) ionization and atmospheric pressure ionization (API). Recent reports show the application of LC/MS to the analysis of taxanes using thermospray ionization, split-flow LC/ES-MS and LC/ES-MS/MS to screen plant or cell culture extracts.

Pharmacokinetic and pharmacodynamic studies of paclitaxel treatment strategies require extensive analyses of biological samples. Evaluation of oral formulations of paclitaxel for bioavailability following oral dosing in animals requires large numbers of analyses of plasma samples. The average sample preparation plus analysis of HPLC takes 30–60 minutes per sample. Accordingly, it would be desirable to significantly reduce the time for sample preparation and analysis in pharmacokinetic and pharmacodynamic studies of paclitaxel treatment strategies.

A widely used technique of quantitation of analyses by HPLC involves the addition of an internal standard to compensate for various analytical errors. With this approach a known compound at a fixed concentration is added to the unknown sample to give a peak in the chromatograph which can be measured separately. This known compound is used as an internal marker to compensate for the effect of minor variations in separation parameters on peak size, including sample-size fluctuations. However, because the delivery of sample volumes is quite precise with microsampling valves, the main utility of the internal standard technique is in assays that require sample pretreatment (and/or solute derivatization) where variable recoveries of compounds of interest may occur.

To compensate for losses of the compound of interest during sample workup, an internal standard that is structurally similar to the compound(s) of interest is added at a known concentration to the original unknown sample, the pretreatment is carried out, and the resulting sample is analyzed. In this approach any loss of the compound of interest will be accompanied by the loss of an equivalent fraction of internal standard. The accuracy of this approach is obviously dependent on the structural equivalence of the compound(s) of interest and the internal standard i.e., for best results the internal standard and the compound(s) of interest should, among other things, extract equally.

The selection of the internal standard is critical for measurements. An internal standard generally must have a completely resolved peak such that there are no interferences; must elute close to compound(s) of interest (similar k' values); must behave equivalently to compound(s) of interest for analyses involving pretreatments derivative formation, etc.; must not be present in the original sample; and must be stable such that it is unreactive with sample components, column packing, or the mobile phase. The internal standard must be added at a concentration that will produce a measurement ratio of about unity with compound (s) of interest, and it is desirable for the internal standard to be commercially available in high purity. More than one internal standard may be required for multicomponent mixtures to achieve highest precision.

A practical problem with the internal standard technique is that the standard must be located in a "vacant" region in the sample analysis. For simple mixtures this is usually not difficult. However, for complex samples the selection of an internal standard can be tedious. A satisfactory internal standard often is a compound that is structurally related to the compound to be measured (e.g., an isomer or close homolog). The internal standard should have similar k', solubility, and detection response but be adequately separated from other sample components.

Accordingly, there remains a need to provide a new and improved internal standard for use with pharmacokinetic and pharmacodynamic studies of paclitaxel treatment strategies, and in particular studies utilizing high performance liquid chromatography/mass spectrometry for analysis of paclitaxel in biological samples. There remains a need for an internal standard of paclitaxel for use in high performance liquid chromatography/mass spectrometry which can significantly reduce the time for sample preparation and analysis. The present invention is directed to meeting these needs by providing stable isotopically labeled taxane analogs, and in particular a carbon-13 labeled paclitaxel, and methods for synthesizing the same.

SUMMARY OF THE INVENTION

It is an object of the present invention to provide a new and useful internal standard compound for use in the analyses of biological samples for taxane concentrations.

It is a further object of the present invention to provide an isotopically labeled paclitaxel useful as an internal standard in high performance liquid chromatography/mass spectrometry.

It is a further object of the present invention to provide paclitaxel molecules labeled with stable isotopes of carbon and/or hydrogen for use in analyses of paclitaxel treatment strategies.

It is further an object of the present invention to provide a method for producing a new internal standard compound useful as an internal standard in the analyses of biological samples for taxane concentrations.

According to the present invention, then, a chemical compound is provided which comprises an isotopically labeled analog of a standard taxane molecule, such as paclitaxel. The isotopically labeled analog is synthetically formed to have incorporated therein at a selected position a stable isotope of an element that exists at the selected position in the standard taxane molecule. The stable isotope is one which has a mass that is different from the mass of the most abundantly occurring isotope of the element in nature, such that the isotopically labeled analog has a molecular weight different from the molecular weight of the standard taxane molecule.

Exemplary stable isotopes include carbon-13 and deuterium, which may be incorporated at selected positions in the A-ring sidechain of the isotopically labeled analog, such as in an aromatic ring. A plurality of stable isotopes, which may be different isotopes or identical isotopes and particularly carbon-13, may be incorporated in the isotopically labeled analog at corresponding selected positions. The molecular weight of the isotopically labeled analog may differ significantly from the molecular weight of the standard taxane molecule, for example by between about 4 and about 10 amu's, and preferably about 6 amu's, such that the isotopically labeled analog is distinguishable by mass spectrometry from the standard taxane molecule.

An isotopically labeled analog according to the present invention may specifically have the formula as follows:

wherein a majority of carbon atoms in the aromatic ring of the 3'-N-benzoyl group are carbon-13 atoms, and particularly where each carbon atom in the aromatic ring of the 3'-N-benzoyl group may be a carbon-13 atom.

The present invention also provides a method of producing an isotopically labeled taxane molecule. The method comprises the steps of acylating a first compound having the formula as follows:

wherein
  $R_1$ is selected from the group consisting of $NH_2$ and $NH_3^+$,
  $R_2$ is selected from the group consisting of an acetyl group and a hydroxyl group, and
  $P_1$ is a hydroxyl protecting group or hydrogen,
with an acylating agent thereby to form an intermediate compound having a C3'-N-acyl group. The acylating agent is synthetically formed to have incorporated therein at a selected position a stable isotope of an element, wherein the stable isotope has a mass different from the mass of the most abundantly occurring isotope of the element in nature. Where $P_1$ is a hydroxyl protecting group, the intermediate compound is thereafter deprotected by replacing $P_1$ with hydrogen to produce the isotopically labeled taxane molecule. When $R_2$ is a hydroxyl group, the method may include the step of selectively acylating the intermediate compound at the C-10 position prior to the step of deprotecting the intermediate compound.

The step of acylating the first compound to form an intermediate compound having a C3'-N-acyl group may be accomplished by acylating the first compound with benzoyl chloride in the presence of triethylamine, wherein a plurality of carbon atoms in the aromatic ring of the benzoyl group of the benzoyl chloride are carbon-13 atoms. Additionally, the first compound may be formed by coupling an active ester of a protected taxane A-ring sidechain acid with a protected taxane backbone to form a coupled product, and thereafter deprotecting the coupled product to form the first compound. The active ester may have a formula as follows:

where CBZ is the carbobenzyloxy group, and the protected taxane backbone may be 7-CBZ baccatin III. The step of deprotecting the coupled product may include hydrogenolytic deprotection at the C-7 position to form a 7-deprotected product, followed by hydrogenolytic deprotection at the 3'-N position to form the first compound.

The present invention is also directed to a method of determining the retention of a target taxane in a biological material derived from an organism that has been dosed with the target taxane. The method comprises the steps of taking a selected test sample of the biological material that contains an unknown amount of the target taxane, adding a known amount of an isotopically labeled internal standard to the test sample, processing the test sample to retrieve the target taxane and the internal standard from the test sample, measuring the amount of the target taxane and the amount of the internal standard retrieved from the test sample, and calculating the amount of the target taxane lost during processing of the test sample based on the amount of the target taxane retrieved from the test sample and the ratio of the amount of the internal standard retrieved from the test sample to the known amount of the internal standard added to the test sample.

A plurality of selected test samples of the biological material may be taken. When paclitaxel is the target analyte, the method preferably includes adding an internal standard that is an isotopically labeled analog of paclitaxel, such as one having a plurality of carbon-13 atoms in the aromatic ring of the 3'-N-benzoyl group. The step of processing may include extracting the target taxane and the internal standard from the test sample by partitioning into methyl-t-butyl ether, and may further include separation by liquid chromatography.

The amount of the target taxane and internal standard may be measured using a mass spectrometer operated in positive ion mode. When the target taxane is paclitaxel, the amount of the target taxane is measured by monitoring the transition from 854.4 amu's to 509.2 amu's in the mass spectrometer. When the internal standard is an isotopically labeled paclitaxel molecule having a molecular weight about six (6) amu's greater than the molecular weight of the target paclitaxel, the amount of the internal standard is measured by monitoring the transition from 860.4 amu's to 509.2 amu's in the mass spectrometer. The amount of the target taxane lost during processing may be calculated by dividing the amount of the target taxane retrieved from the test sample by the ratio of the amount of the internal standard retrieved from the test sample to the known amount of the internal standard added to the test sample.

These and other objects of the present invention will become more readily appreciated and understood from a consideration of the following detailed description of the exemplary embodiments of the present invention when taken together with the accompanying drawings, in which:

DETAILED DESCRIPTION OF THE EXEMPLARY EMBODIMENTS

The present disclosure is broadly directed to new chemical compounds, namely stable isotope labeled taxanes. In particular, the present invention provides isotopically labeled analogs of standard taxanes, wherein a given isotopically labeled analog has incorporated therein at a selected position in the structure thereof a stable, or non-radioactive, isotope having a mass different from the mass of the most abundantly occurring isotope of the appropriate element in nature. A given analog can be differentiated from its corresponding standard taxane (one having primarily only the most naturally abundant isotopes incorporated therein) using methods such as mass spectrometric analysis, given the molecular weight differences between the isotopically labeled analog and its corresponding standard taxane.

The natural abundance of various isotopes in nature has been approximated, for example, in the CRC Handbood of Chemistry and Physics, published by CRC Press, Inc. The most abundantly occurring form of carbon, the carbon-12 ($^{12}C$) isotope, is approximately 98.90% abundant in nature. The stable carbon-13 ($^{13}C$) isotope, by contrast, is only approximately 1.10% naturally abundant. Other isotopes of carbon are even less abundant, and many undergo radioactive decay. The most abundantly occurring isotope of hydrogen ($^1H$) is approximately 99.985% abundant in nature. The stable isotope deuterium ($^2H$), by contrast, is only approximately 0.015% naturally abundant. Various stable isotopes of nitrogen and oxygen exist in nature, as well. For example, $^{14}N$ and $^{15}N$ are 99.63% and 0.37% naturally abundant, respectively; $^{16}O$, $^{17}O$ and $^{18}O$ are 99.76%, 0.04% and 0.20% naturally abundant, respectively.

Accordingly, standard taxane molecules known in the art will generally have incorporated therein various isotopes in these respective percentages of natural abundance. The present invention, however, provides analogs of such standard taxanes in which the less naturally abundant stable isotopes are selectively incorporated into the taxane structure at desired positions thereof, such that a given analog will have a characteristic molecular weight different from the molecular weight of its corresponding standard taxane.

While the preferred form of the invention is directed to a carbon-13 labeled paclitaxel, it should be appreciated that the present invention contemplates various forms of stable isotope labeled taxanes, such as carbon-13 and/or deuterium labeled paclitaxel, docetaxel, and analogs and derivatives thereof. In particular, chemical compounds are contemplated wherein various sites of the paclitaxel or docetaxel 13-sidechains are labeled with stable isotopes of carbon, hydrogen, nitrogen or oxygen. In addition, other taxane compounds are contemplated in which various functional groups of taxane molecules, such as the C4 or C10 acetates or the C2 benzoate, are labeled with such stable isotopes. It should further be noted that, while the present invention contemplates taxane compounds labeled with deuterium, the tendency of deuterium isotopes to undergo proton exchange with $^1$H weighs in favor of labeling such compounds with isotopes of elements that are less subject to exchange, such as $^{13}$C.

The present invention also concerns methods of producing stable isotope labeled taxanes, and a carbon-13 labeled paclitaxel in particular. In addition, it should be appreciated that stable isotope labeled paclitaxels may be produced according to other known synthetic procedures, wherein a standard reactant in the synthesis is replaced with a corresponding isotopically labeled reactant. Such synthetic processes generally include attaching an appropriate A-ring side chain to the C13 site of a baccatin III or 10-deacetyl baccatin III backbone. Various protecting groups, deprotections and substitutions may be used to improve efficiency, yield, cost and like considerations. Exemplary semi-synthetic methods useful in forming paclitaxel, docetaxel and analogs and derivatives thereof may be found, for example, in U.S. Pat. Nos. 5,770,745; 5,939,566; 5,675,025; 5,688,977; 5,750,736; 5,750,737; 5,914,411; and 6,048,990.

The stable isotope labeled compounds of the present invention are demonstrably useful for improving the efficiency of methodologies for analysis of biological samples for taxane concentrations. In particular, the carbon-13 labeled paclitaxels of the present invention are especially useful compounds in the analysis of biological tissue samples for taxane concentrations in pharmacokinetic and pharmacodynamic studies. The isotopically labeled taxanes of the present invention may replace currently used taxane internal standards, such as Taxol C (Taxol® is a registered trademark of Bristol-Myers Squibb Company).

Figure 1:
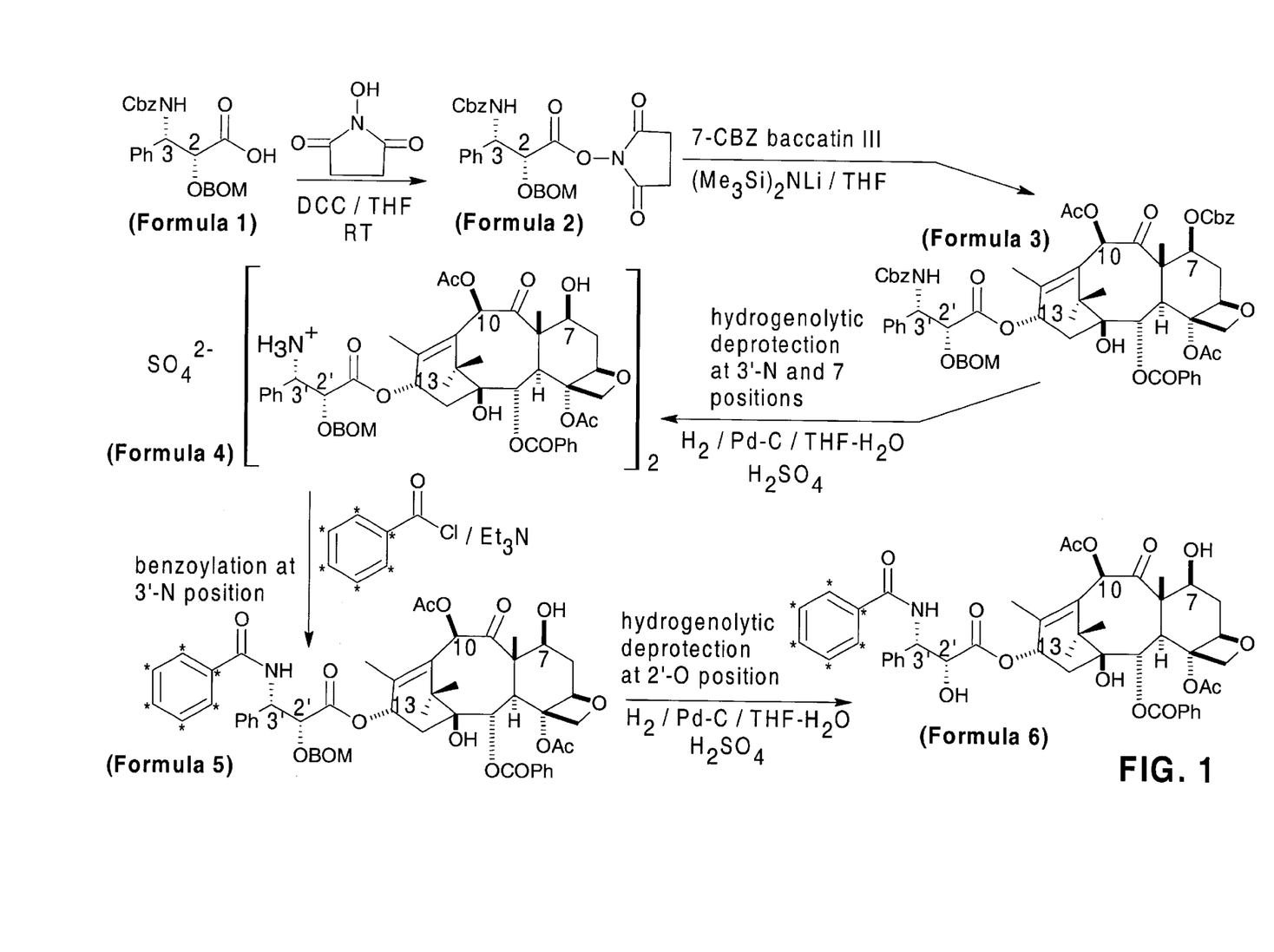
FIG. 1 shows an exemplary semi-synthetic preparation of a carbon-13 labeled paclitaxel.

An exemplary preparation of a carbon-13 labeled paclitaxel is outlined in FIG. 1. This process generally includes the steps of forming an active ester of a protected paclitaxel sidechain acid, coupling the active ester with a protected baccatin III or 10-deacetylbaccatin III taxane backbone, deprotecting the taxane backbone, deprotecting the side chain nitrogen, acylating the side chain nitrogen with an appropriate stable isotope labeled acylating agent, acylating at C10 when appropriate, and further deprotecting the side chain hydroxyl. It should be appreciated that variations to this process may include using a stable isotope labeled acylating agent for the C10 acylation, rather than or in addition to the side chain nitrogen acylation, or using a stable isotope labeled side chain precursor for use in the formation of the active ester. Other variations are contemplated by the present invention.

The exemplary method of producing a compound according to the present invention, wherein the phenyl ring of the 3'-N-benzoyl group is preferably uniformly carbon-13 labeled, starts with a compound that is a phenylisoserine derivative, which is coupled to the 13-hydroxyl group of a 7-hydroxyl protected baccatin III. A four-step conversion of the phenylisoserine derivative and 7-CBZ-baccatin III to carbon-13 labeled paclitaxel was performed via active ester coupling, hydrogenolytic deprotection of the coupled ester at the 7-O and 3'-N positions (formation of 2'-O-BOM amine) followed by N-benzoylation of the free 3'- amino intermediate with carbon-13 labeled benzoyl chloride (formation of 2'-O-BOM-paclitaxel-$^{13}$C) and hydrogenolytic deprotection of the N-benzoylated product at the 2'-O position to form paclitaxel-$^{13}$C.

Specifically, the N-succinimidyl active ester was obtained by esterification of the protected acid with N-hydroxysuccinimide in the presence of DCC and the crude product was purified by crystallization. The purified active ester was coupled with 7-CBZ-baccatin III in the presence of lithium bis(trimethylsilyl)amide and the crude material was purified by normal phase column chromatography. The purified coupled ester was hydrogenated to the free amine intermediate, which without isolation was N-benzoylated with carbon-13 labeled benzoyl chloride (benzoyl chloride-ring-UL-$^{13}$C) in the presence of triethylamine. The mixture was hydrogenated and the crude product purified by crystallization and by reverse phase column chromatography which provided 99.5% purity paclitaxel-$^{13}$C (by HPLC area %). The exemplary process is described in detail as follows.

1. Production of the Protected 3-Phenylisoserine Side Chain

The production of a C3-N-CBZ, C2-benzyl-type protected (2R,3S)-3-phenylisoserine side chain has been previously disclosed in U.S. Pat. No. 5,684,175 to Sisti et al., entitled "C-2' Hydroxyl-Benzyl Protected, N-Carbamate Protected (2R,3S)-3-Phenylisoserine and Production Process Therefor". This compound has the general formula:

Here, the $P_1$ protecting group on the 2-hydroxyl is a hydrogenatable protecting group such as benzyloxymethyl (BOM) or benzyl. The preferred compound for use with the present invention is a (2R,3S)-2-O-benzyloxymethyl-3-N-carbobenzyloxy-3-phenylisoserine acid (Formula 1, $C_{25}H_{25}NO_6$, MW: 435.5) as follows:

(Formula 1)

It should be appreciated that alternative embodiments of the present invention contemplate the use of a stable isotope labeled 3-phenylisoserine acid, such as one in which various carbon atoms of the 3-phenyl group are carbon-13 atoms or in which various hydrogen atoms on the paclitaxel side chain are deuterium atoms, or in which the nitrogen and oxygen positions may be labeled with stable isotopes of those elements.

2. N-Succinimidyl Active Ester of the Protected 3-phenylisoserine Side Chain Acid In the preferred process, an N-succinimidyl active ester of the protected acid is formed as follows from the protected 3-phenylisoserine side chain:

(Formula 1)

(Formula 2)

Here, a (2R,3S)-2-O-benzyloxymethyl-3-N-carbobenzyloxy-3-phenylisoserine (Formula 1), is reacted with N-hydroxy-succinimide in the presence of dicyclohexylcarbodiimide (DCC) and tetrahydrofuran (THF) at room temperature to form a (2R,3S)-2-O-benzyloxymethyl-3-N-carbobenzyloxy-3-phenylisoserine N-succinimidyl ester (Formula 2, $C_{29}H_{28}N_2O_6$, MW: 532.6).

To a solution of 34.20 g of the protected acid in 40 mL of anhydr.THF was added 8.77 g (73.9 mmol) of N-hydroxysuccinimide and the resulting mixture was stirred under nitrogen at 45°–50° C. (water bath) until a homogenous solution was obtained (~20 minutes). To the stirred solution under nitrogen was added a solution of 16.77 g (81.3 mmol) of DCC in 20 mL of anhydr. THF over 15 minutes. During the addition of DCC solution and for 30 minutes after, the reaction flask was immersed in a cold water bath (~10° C. The dense, heterogenous reaction mixture was diluted with 50 mL of anhydr. THF, stirred for an additional 3 hours and diluted with 500 mL of ethyl acetate, stirred for 10 minutes and filtered.

The resulting dicyclohexylurea (DCU) filter cake was washed with 2×100 mL of ethyl acetate and washes were combined with the original filtrate. After evaporation of solvent under reduced pressure, the resulting solid was dried in a vacuum oven at RT for 2 h to give 28.90 g of crude N-succinimidyl active ester. The DCU cake was stirred with 300 mL of ethyl acetate for 15 hours and the solid was isolated by filtration. The solid was washed on the filter with 300 mL of fresh ethyl acetate and dried in a vacuum oven at RT for 2 h to give 16.04 g of a white material. The filtrate and wash were combined and evaporated under reduced pressure.

The resulting solid was dried in a vacuum oven at RT for 2 h and gave an additional 12.66 g of the active ester. The two portions of the product were combined, dissolved in 700 mL of ethyl acetate, the solution was filtered and placed in a refrigerator for 14 hours. The obtained solid was filtered, washed with 50 mL of cold ethyl acetate/heptane mixture 1:1 (v/v) and dried in a vacuum oven at RT for 22 h to give 26.29 g of the white crystalline product. The product was dissolved in 450 mL of ethyl acetate containing 5% THF and the resulting solution was stirred in ice-bath for 4 hours. The crystallized solid was filtered, washed with 25 mL of ethyl acetate/heptane mixture 1:1 (v/v), with 100 mL of heptane and dried in a vacuum oven at RT for 6 hours to give 21.02 g of the active ester product (>97% purity by HPLC).

The present invention contemplates the use of various other active esters, in addition to the N-succinimidyl active ester described above. Exemplary active esters that may be used with the method of the present invention are described with reference to U.S. patent application Ser. No. 09/336,961, now U.S. Pat. No. 6,136,999 and U.S. patent application Ser. No. 09/336,962, now U.S. Pat. No. 6,143,902.

3. Production of C7-CBZ Protected Baccatin III

The N-succinimidyl active ester must be coupled with a suitable taxane backbone, which is preferably a protected baccatin III backbone, and in particular C-7 CBZ protected baccatin III. It should be appreciated, however, that other suitable taxane backbones for use with the present invention include protected 10-deacetyl baccatin III backbones, and in particular C-7, C-10 di-CBZ 10-deacetyl baccatin III, which has been previously disclosed in U.S. Pat. No. 5,688,977 and U.S. patent application Ser. No. 08/616,466, now U.S. Pat. No. 6,107,497.

Two alternative routes may be used for producing C-7 CBZ protected baccatin III having the formula as follows:

where CBZ is the carbobenzyloxy group, $CO_2CH_2Ph$.

On one hand, baccatin III can be protected at the C-7 site to yield C-7 CBZ baccatin III. On the other hand, 10-deacetylbaccatin III (10-DAB III) can be directly converted to C-7 CBZ baccatin III without going through a baccatin III intermediate. Production from baccatin III is advantageous for its yield and simplicity. The method using 10-deacetylbaccatin III has an advantage since 10-deacetylbaccatin III is much more naturally abundant, and thus less expensive, than baccatin III. Alternatively, 10-deacetyl baccatin III can be first converted to baccatin III according to the procedures described in U.S. Pat. Nos. 5,750,736 and 5,914,411.

The production of C-7-CBZ protected baccatin III has been previously disclosed in U.S. Pat. Nos. 5,750,737 and 5,973,170, and in U.S. patent application Ser. No. 08/922,684, now U.S. Pat. No. 6,133,462.

Route I (Using baccatin III) C-7 CBZ baccatin III has the formula:

and can be synthesized from baccatin III according to the following reaction:

baccatin III

C-7 CBZ baccatin III 10-deacetyl baccatin III

C-7 CBZ baccatin III

Baccatin III is dissolved in anhydrous THF (tetrahydrofuran) to form a first solution, which is cooled under a nitrogen atmosphere to a reduced temperature of less than −20° C. n-Butyl lithium (1.6 M in hexane) is then added dropwise to the first solution to form a second solution, which is stirred for approximately five minutes at the reduced temperature. This creates the C-7 lithium alkoxide of baccatin III:

where $M^+$ is $Li^+$, and R is $CH_3$. Alternatively, other C-7 metal alkoxides of baccatin III may be formed as taught in U.S. Pat. No. 5,973,170.

Benzyl chloroformate (CBZ-Cl) is added dropwise to the second solution to form a third solution which is then stirred and allowed to warm to 0° C. over approximately one hour. The third solution is quenched with cold saturated ammonium chloride to eliminate any excess n-butyl lithium and CBZ-Cl, and the mixture is concentrated under vacuum to yield a first residue. This first residue is next taken up in ethyl acetate and washed once with water to remove unwanted salts. Next, the residue is washed with brine. The organic layer is then dried and concentrated under vacuum to yield a second residue. The second residue is recrystallized or column chromatographed with ethyl acetate:hexane to give C-7 CBZ baccatin III as a white solid.

Route 2 (Using 10-deacetylbaccatin III)

Alternatively, C-7 CBZ baccatin III can be synthesized directly from 10-deacetylbaccatin III as follows:

Here, 10-DAB III is dissolved in THF to form a first solution which is cooled to a reduced temperature of less than −20° C. under a nitrogen atmosphere. At least two equivalents of n-butyl lithium (1.6 M in hexane) are then added dropwise to the first solution to form a second solution which is then stirred for approximately five minutes at the reduced temperature. Preferably, acetyl chloride (one equivalent) is added to the second solution to form a third solution which is stirred at the reduced temperature for approximately thirty minutes. Alternatively, acetic anhydride (one equivalent) may possibly be used in place of the acetyl chloride to acylate the 10-DAB III.

In either case, benzyl chloroformate (one equivalent) is next added, and this fourth solution is stirred for an additional thirty minutes at the reduced temperature and then warmed to 0° C. over thirty minutes. The fourth solution is then quenched with cold saturated ammonium chloride at the reduced temperature to remove any excess n-butyl lithium, acetyl chloride and CBZ-Cl; this mixture is then warmed to room temperature. The solvent is removed under vacuum to yield an initial residue which is taken up in ethyl acetate and washed with water to remove unwanted salts. The residue is then washed with brine, dried and concentrated under vacuum to yield a final residue. The final residue is chromatographed (silica gel, hexanes: ethyl acetate) to yield C-7-CBZ baccatin III. It is important to note that this method represents a direct synthesis of C-7-CBZ baccatin III from 10-DAB III, as the intermediate formed in this reaction is a C-7 lithium alkoxide of baccatin III; that is, the intermediate is not baccatin III itself.

4. Esterification of C-7-CBZ Baccatin III and the Side Chain

The N-succinimidyl active ester is next coupled with the 7-CBZ baccatin III taxane backbone to form the N-debenzoyl-7-O,N-di(carbobenzyloxy)-2'-O-(benzyloxymethyl) paclitaxel coupled ester (Formula 3, $C_{64}H_{67}NO_{18}$, MW: 1138.2) as follows:

(Formula 2) + ... → (Me₃Si)₂NLi/THF → (Formula 3)

To a stirred solution of 16.30 g of N-succinimidyl ester of the protected acid and 20.01 g of 7-CBZ-baccatin III in 250 mL of anhydr. THF was added 70 mL of 1M solution of lithium bis(trimethylsilyl)amide in THF (70 mmol) over 10 minutes at ~20° C. under $N_2$ atmosphere. The slight exotherm of the reaction was controlled by immersing the reaction flask during addition of base in a cold water bath (~10° C.). The reaction mixture was stirred for 1 h and 45 minutes, diluted with 1 L of ethyl acetate/water mixture 1:1 (v/v) and stirred again for 10 minutes. The organic phase was separated, washed with 4×250 mL of water followed by 250 mL of brine, dried with 20 g of anhydr. magnesium sulfate and filtered. The filtrate was evaporated under reduced pressure and the resulting solid was dried in a vacuum oven at RT for 17 h to give 32.04 g of the crude coupled ester (HPLC: 75.4% of the product, 17.1% of 7-CBZ-baccatin III and 0.2% of the 2'-epimer; HPLC method: SSCoupling).

The crude coupled ester (TLC and HPLC analysis) 27.96 g of solid material, was purifed by column chromatography, using silica and cyclohexane containing 1% acetic acid/IBAc=3:2 (v/v) as an eluent to give 20.95 g of the pure coupled ester, free of the starting 7-CBZ-baccatin III.

The product (20.95 g) was dissolved in 55 mL of methyl tertiary butyl ether (MTBE) at 50° C. and the resulting solution was stirred at RT for 20 minutes (crystallization was started) and then in an ice-bath for 1 hour. The crystalline solid was filtered, washed with 40 mL of cold MTBE and dried in a vacuum oven at 40° C. for 8 hours to give 17.89 g of the product. The product was dissolved in 100 mL of ethyl acetate at 55° C. and to the stirred, warm solution was added slowly 40 mL of heptane (crystallization initiated) and after 10 minutes was added an additional 10 mL of heptane and the mixture was stirred 20 minutes at RT and then 1.5 hours in an ice bath.

The crystalline solid was filtered, washed with 50 mL of heptane and dried in a vacuum oven at 40° C. for 5 hours to give 16.91 g of the product. The product was dissolved again in 110 mL of ethyl acetate at 55° C. and the clear, warm solution was carefully filtered through a sintered glass funnel. To the stirred filtrate was added 50 mL of heptane (crystallization was started), stirred for 10 minutes, then was added an additional 20 mL of heptane and the mixture was stirred 10 minutes at RT and then 1 hour in an ice bath. The crystalline solid was filtered, washed with 50 mL of heptane and dried in a vacuum oven at 40° C. for 15 hours to give 16.08 g of the product (purity by HPLC:>99%).

It should also be appreciated that the side chain acid may be directly coupled to the protected taxane backbone, without first forming the active ester of the side chain acid. Exemplary processes in which a taxane A-ring sidechain acid is condensed with a protected baccatin III or 10-deacetyl baccatin III backbone are taught in U.S. Pat. Nos. 5,770,745, 5,939,566, 5,948,919, 5,688,977, 5,750,737, and 6,048,990.

5. Deprotection at 3'-N and C-7 Positions and Benzoylation at 3'-N position

The CBZ protecting groups on the 3'-N and C-7 positions are next removed to form the N-debenzoyl-2'-O-(benzyloxymethyl) paclitaxel sulfate (Formula 4, $C_{48}H_{55}NO_{14}$, MW: 870.0), and a carbon- 13 labeled benzoyl group is attached to the 3'-N position to form the 2'-O-(benzyloxymethyl)-carbon-13 labeled paclitaxel (Formula 5, $C_{55}H_{59}NO_{15}$, MW: 980.2, *=$^{13}$C), as follows:

where a carbon atom having a * adjacent thereto in the chemical formulas indicates a carbon-13 isotope.

To a solution of 14.03 g of the coupled ester of Formula 3 (12.33 mmol) in 126 mL of THF was added a solution of 644 mg of 96% sulfuric acid (6.30 mmol) in 9.8 mL of water followed by addition of 8.40 g of 10% Pd/C/50% $H_2O$. The resulting mixture was hydrogenated under balloon hydrogen pressure at RT for 5 hours. Hydrogen was replaced with an atmosphere of nitrogen and to the stirred reaction mixture was added 3.50 mL (25 mmol) of triethylamine followed by addition of 1.50 g (10.23 mmol) of carbon-13 labeled benzoyl chloride. The resulting reaction mixture was stirred for 1.5 hours and filtered through a plug of 100 g silica gel with 20 g of Celite® on the top to remove catalyst.

The plug was washed with 6×150 mL of THF and the original filtrate and the first 450 mL of washes were combined and evaporated under reduced pressure. The resulting solid was dissolved in 200 mL of isobutyl acetate (IBAc) and the solution was washed with 50 mL of 1.5% aqueous HCl. A white solid was precipitated and an attempt to dissolve it by addition of 100 mL of water and extra 50 mL of 1.5% of aqueous HCl failed.

The resulting heterogenous mixture was filtered through a sintered glass funnel, the filtrate was washed with 5×100 mL of water, 100 mL of brine, dried with anhydrous magnesium sulfate, filtered and evaporated under reduced pressure (10.61 g). The resulting solid was dissolved in 200 mL of IBAc/cyclohexane=4:1 (v/v) mixture and the solution was passed through a preconditioned silica plug (60 g $SiO_2$, 3×9 cm) which was then washed with 9×200 mL of IBAc/cyclohexane=4:1 (v/v) mixture. The original filtrate and the first 1200 mL of washes were combined, evaporated under reduced pressure and the resulting solid was dried in a vacuum oven at 40° C. for 6 hours to give 9.97 g of product.

It should be appreciated that when a C7, C10 di-protected taxane backbone is utilized, such as a C7, C10 di-CBZ 10-deacetyl baccatin III, the protecting groups at the 7 and 10 positions and at the 3'-N position may be removed according to the teachings of U.S. Pat. No. 5,688,977 to first form an amine, to which a benzoyl group may be attached at the 3'-N position, followed by C-10 acylation, in the case of paclitaxel, or to which a t-BOC group may be attached at the 3'-N position in the case of docetaxel, for example.

The carbon-13 labeled benzoyl chloride was obtained from Isotech, Inc., located at 3858 Benner Rd., Miamisburg, Ohio 45342. Various reagents labeled with stable isotopes are generally available in the art, and particular compounds having desired isotopes incorporated therein may generally be obtained by the ordinarily skilled artisan. Other suppliers from whom such compounds may be obtained include Sigma-Aldrich Chemicals, located in Milwaukee, Wis. The preferred benzoyl chloride for use in the present invention has a phenyl ring which is uniformly labeled with carbon-13, such that all six carbon positions in the phenyl ring have carbon-13 atoms.

It should be appreciated, however, that the present invention contemplates variations in the stable isotope labeling of taxanes according to the present invention, such as paclitaxel, docetaxel and analogs and derivatives thereof. For example, as indicated above, the β-amino acids for use in forming the A-ring taxane sidechain may incorporate the stable isotopes carbon-13 and deuterium in place of $^{12}C$ and $^{1}H$ atoms at selected positions in the structure thereof, such as at various positions in the 3-phenyl ring of the 3-phenylisoserine acid. Additionally, the present application contemplates variations in the placement of isotopes in the benzoyl group (in the case of paclitaxel), or in other groups, such as the tert-butoxycarbonyl group in the case of docetaxel. For example, the phenyl ring in the benzoyl group may have less than all carbon positions labeled with carbon-13 and/or may have some or all hydrogen positions labeled with deuterium. Additionally, isotopes of other elements may be incorporated into appropriate positions, such as the 3'-nitrogen position and the various oxygen positions in the structure of a selected taxane.

The present invention also contemplates that stable isotopes may be incorporated into a selected taxane at various functional groups on the taxane backbone, such as the C4 and C10 acetate groups or the C2 benzoate group, using synthetic procedures known in the art. For example, an isotopically labeled C10 acetate group may be incorporated by acylating 10-deacetyl baccatin III or a C2'-O-protected 10-hydroxy taxol at the C10 position with an isotopically labeled acylating agent using the synthetic processes disclosed in U.S. Pat. Nos. 5,750,736, 5,914,411, 6,048,990, and 6,066,749.

The ordinarily skilled person will appreciate that in any such sample of a given reagent, such as benzoyl chloride, not all molecules will be identically labeled due to difficulties in synthetically forming such molecules. That is, it should be understood that the replacement of $^{12}C$ atoms with $^{13}C$ atoms, or of $^{1}H$ atoms with $^{2}H$ atoms, may not be accomplished to perfection in any given molecule, such that positions in some molecules in the sample may have isotopes of the given element other than the desired isotope. It is contemplated, however, that a majority of the molecules in a given sample will be labeled with the selected isotope at a common position in the structure thereof. For example, in the case of the preferred carbon-13 labeled paclitaxel according to the present invention, it is contemplated that a majority of the paclitaxel molecules will have a 3'-N-benzoyl group wherein the phenyl ring thereof is uniformly labeled with carbon-13 atoms such that all six carbon positions in the phenyl ring have carbon-13 atoms.

It should additionally be appreciated that when a protected 10-deacetyl baccatin III, such as C7, C10 di-CBZ 10-deacetyl baccatin III, is used as the taxane backbone for the coupling step above, it may be necessary at this point in the synthesis to acylate at C10 to add an acetyl group when paclitaxel or an analog or derivative thereof is the desired end product. Exemplary processes for selectively acylating a 2'-O-protected 10-hydroxy paclitaxel at the C10 position thereof are described in U.S. Pat. Nos. 6,048,990, and 6,066,749. When docetaxel or an analog or derivative thereof is the desired end product, it is unnecessary to acylate at C10, given the free hydroxyl group at the C10 position in the docetaxel structure.

It should further be appreciated that, while the preferred embodiment uses a benzyl-type protecting group (such as BOM, benzyl or benzoyl) at C2' such that the C2' position remains protected during acylation of the C3'-N site, certain protecting groups for use at the C7, C10 and 2' positions may be removed simultaneously as taught in U.S. Pat. Nos. 5,770,745, 5,939,566 and 6,072,060, for example. As such, the step of acylating the C3'-N site may be accomplished when the C2' site is unprotected (i.e. when a hydroxyl group is present at the C2' site).

6. Removal of the 2'-O Protecting Group

Finally, in the preferred process, the protecting group at the C2' position is removed thereby to form the final carbon-13 labeled paclitaxel product (Formula 6, $C_{47}H_{51}NO_{14}$, MW: 859.9), as follows:

(Formula 5)

(Formula 6)

Exemplary processes for the removal of a C2' benzyl-type protecting group, such as benzyloxymethyl or benzyl, are described in U.S. Pat. Nos. 5,675,025, 5,688,977, and 5,750,737.

Here, to a solution of 9.97 g of 2'-O-BOM -paclitaxel-$^{13}$C (10.17 mmol) in 100 mL of THF was added a solution of 521 mg of 96% sulfuric acid (5.10 mmol) in 1.5 mL of water followed by addition of 20.01 g of 10% Pd/C/50% $H_2O$. The resulting mixture was hydrogenated under balloon hydrogen pressure at RT for 3.5 hours. Hydrogen was replaced with an atmosphere of nitrogen and the reaction mixture was filtered through Celite® (20 g) to remove catalyst. The Celite®/catalyst cake was washed with 600 mL of ethyl acetate. The original filtrate and washes were combined and partitioned with 5×150 mL of water, 1×150 mL of brine, dried with anhydrous magnesium sulfate and filtered. The filtrate was evaporated under reduced pressure and the resulting solid was preliminarily dried (2 h/40° C./22 torr/, rotavap) to give 8.64 g of the product (93.4% of paclitaxel-$^{13}$C by HPLC).

The product (8.64 g) was dissolved in 25 mL of ethyl acetate at 50° C. and to the stirred solution held at the same temperature was added 20 mL of cyclohexane to produce a permanent turbidity of the mixture. The mixture was stirred at RT for 20 minutes and then 1 hour in an ice-bath to precipitate solid. The solid was filtered and washed with 60 mL of cold ethyl acetate/cyclohexane 1:1 (v/v) mixture then with 20 mL of heptane and dried in a vacuum oven at RT for 4 h to give 6.24 g of the product (paclitaxel-$^{13}$C, ~97% purity by HPLC).

The product (6.24 g) was dissolved at 50° C. in 90 mL of ethanol, the resulting solution was filtered through a 3 piece fritted filter using 0.2 μm filter and the filtrate was concentrated under reduced pressure (rotavap) to ~60 mL. To this stirred solution at 50° C. was added slowly 10 mL of water and the crystallizing mixture was stirred at RT for 1 hour and then kept in freezer for 15 hours. The solid was filtered, washed with 7 mL of cold ethanol/water=7:3 (v/v) mixture and then dried in a vacuum oven at 50° C. for 6 h to give 5.96 g of (paclitaxel-$^{13}$C, >97% purity by HPLC).

The product (5.88 g) was repurified using reverse phase column chromatography with a mixture of 70% of methanol, 30% of water and ~0.1% of acetic acid as the mobile phase (v/v/v). The mother liquors from first and second crystallization were evaporated and combined (2.01 g) and purified separately utilizing the same chromatographic conditions. On the basis of UV trace and TLC analysis, fractions from both column purifications were pooled together. After controlled removal of methanol by rotary evaporation, the resulting suspension was filtered and the solid was dried in a vacuum oven (40° C. for 19.5 hours and 60° C. for 1 hour under nitrogen purge at 50 mL/min) to give 6.01 g of the pure product (99.5% of paclitaxel-$^{13}$C, by HPLC).

Mass Spectrometry

The use of the isotopically substituted analog of paclitaxel in a mass spectrometric assay offers significant advantages over currently used chemical analogs. In particular, the use of an isotopically labeled paclitaxel of Formula 6 according to the present invention offers increased throughput (shortened analysis time) and improved accuracy over previously used internal standards such as Taxol C.

As mentioned above, an isotopically labeled internal standard will always contain a small amount of unlabeled material, and the amount of unsubstituted paclitaxel present in the internal standard will set a lower limit to any assay using the standard. To achieve lower limits of quantitation with a significantly contaminated internal standard requires using a lower internal standard concentration. This, in turn, raises the uncertainty of measurement of the internal standard itself. This same argument applies to a chemical analog internal standard, whether synthesized or obtained from a natural source. In either case the result is the same; the lower the contamination of the internal standard with the target analyte, the more accurate the analysis can be, and the lower the limit of quantitation can be set.

The singly charged protonated molecular ion of paclitaxel has a base mass of 854.3 atomic mass units (amu); The paclitaxel-$^{13}$C of Formula 6 according to the present invention (incorporating six $^{13}$C atoms per molecule) has a base mass of 860.4 amu; Taxol C has a base mass of 848.4 amu. All three give a strong product ion at 509.2 amu, which is used for quantitation.

The pure paclitaxel-$^{13}$C was tested for presence of unsubstituted paclitaxel by combined liquid chromatography/triple quadrupole mass spectrometry. The current internal standard, Taxol C, was then compared under identical conditions. Under assay conditions, paclitaxel and paclitaxel-$^{13}$C both elute at just under 3 minutes, while Taxol C elutes at 3.5 minutes. Paclitaxel, Paclitaxel-$^{13}$C and Taxol C were all quantitated by multiple reaction monitoring (MS/MS) using the common fragment ion at 509.2 amu.

Figure 2:
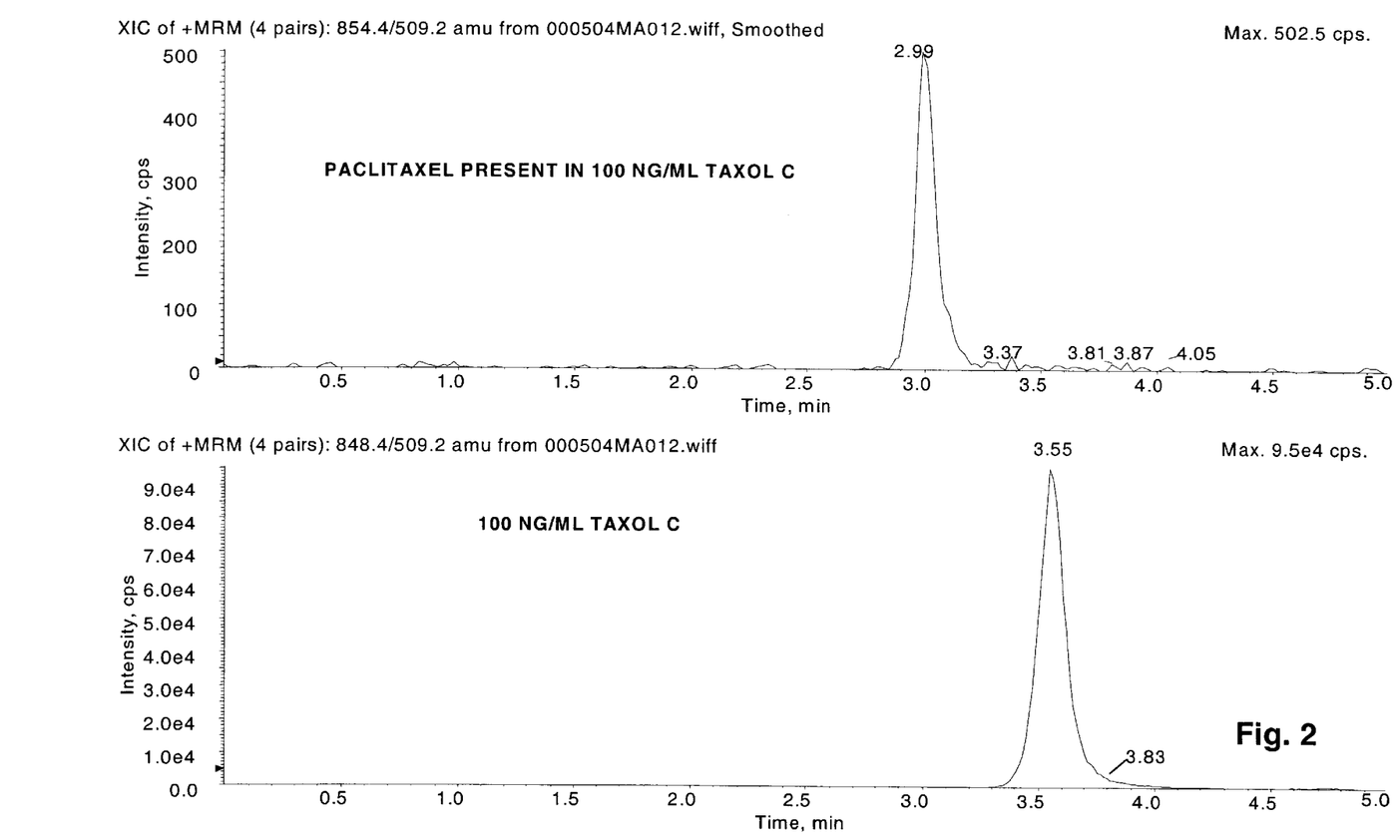
FIG. 2 is a graph of the results from a mass spectrometric analysis of a liquid chromatography aliquot of paclitaxel C.

FIG. 2 shows the results from analysis of an aliquot of Taxol C. The lower trace is the response of Taxol C; the upper trace is that of paclitaxel present in Taxol C. It should be noted that the intensity scales of the upper and lower traces are substantially different, such that the intensity of paclitaxel is minimal relative to that of Taxol C. The average of multiple analyses indicates that paclitaxel is present at a concentration of 0.5%.

Figure 3:
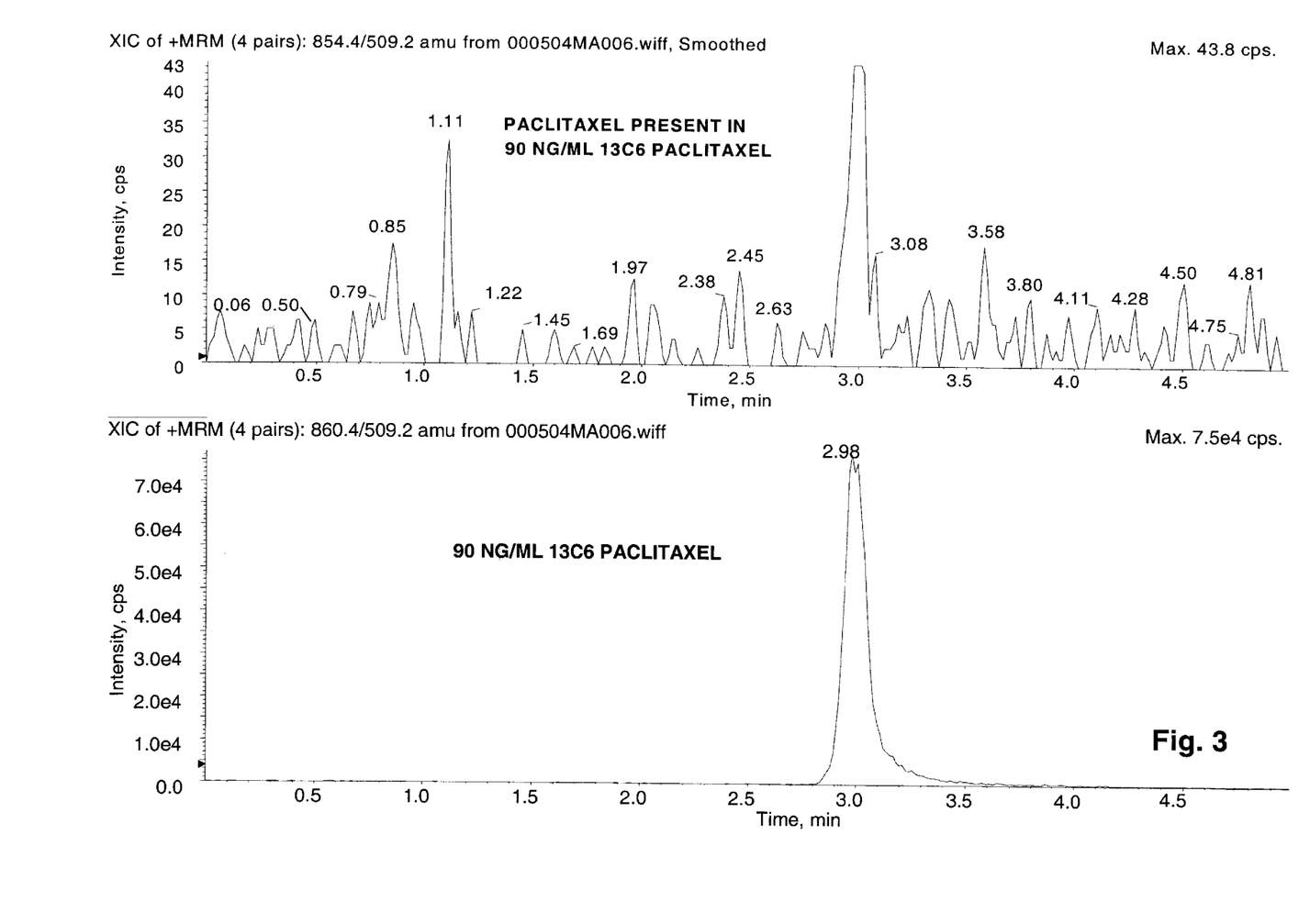
FIG. 3 is a graph of the results from a mass spectrometric analysis of a liquid chromatography aliquot of a carbon-13 labeled paclitaxel according to the present invention.

FIG. 3 shows the results from analysis of an aliquot of paclitaxel-$^{13}$C according to Formula 6 of the present invention. The lower trace is the response of paclitaxel-$^{13}$C; the upper trace is that of paclitaxel present in paclitaxel-$^{13}$C. Again, it should be noted that the intensity scales of the upper and lower traces are substantially different, such that the intensity of paclitaxel is minimal relative to that of paclitaxel-$^{13}$C. The average of multiple analyses indicates that paclitaxel is present at a concentration of 0.05%.

Accordingly, the proportion of target analyte (paclitaxel) in paclitaxel-$^{13}$C is approximately ten times lower than in Taxol C (0.05% versus 0.5%, respectively). All things being equal, this translates to being able to achieve a ten times lower limit of quantitation with the same accuracy of measurement of the internal standard, by using the paclitaxel-$^{13}$C according to Formula 6 of the present invention produced by the method described above.

An additional benefit offered by all isotopically labeled analog internal standards is that their chemical properties are essentially identical to the target analyte. This means that during sample extraction and workup there can be no or very little differential loss of internal standard versus the target analyte due to differing chemical properties, as may be the case with a chemical analog with differing chemical properties. Again, this translates to an inherently more accurate analytical method when using paclitaxel-$^{13}$C as an internal standard, versus using Taxol C (or any other chemical analog), in pharmacokinetic and pharmacodynamic studies of paclitaxel.

Isotopically labeled taxane analogs according to the present invention preferably differ from their corresponding standard taxanes by a molecular weight of between 4 and 10 amu's. In particular, it is desirable that isotopes be incorporated in such a manner, and the mass difference be sufficient such that, the mass spectrometric molecular ion peaks of the analog and standard taxane are distinguishable. It should be understood that the present invention contemplates that smaller mass differences may be readily distinguishable as the state-of-the-art in mass spectrometry equipment and resolution improves.

Analytical Method

Previously, analyses of samples for paclitaxel and hydroxylated metabolite content had a limit of quantitation of 3 ng/ml using LC/MS/MS to detect paclitaxel, 6-alpha-hydroxy paclitaxel and 3'-para-hydroxy paclitaxel. Those analyses used Taxol C as the internal standard, with a 75×4.6 mm HPLC column.

The present invention achieved significantly lower quantitation limits by using the high-purity isotopically-substituted paclitaxel according to Formula 6 of the present invention. In addition, the prior HPLC column was replaced with a narrow bore 50×2.1 mm column, the flow rate was lowered and mobile phase, mass spec and interface parameters were optimized. Use of a short, narrow-bore LC column minimizes matrix effects seen near the void volume which can reduce method sensitivity. These improvements resulted in lowering the limit of quantitation thirty-fold, to 0.100 ng/ml paclitaxel.

An exemplary quantitation using the paclitaxel-$^{13}$C according to Formula 6 of the present application is as follows. An accurately measured aliquot (0.4 ml dog plasma in a 2 ml microfuge tube) of a sample containing an unknown amount of paclitaxel is spiked with a known amount (1.5 to 10 ng/ml, and preferably 2 ng/ml) of paclitaxel-$^{13}$C (Formula 6). The compounds are next extracted from the sample by partitioning into methyl-t-butyl ether. Here, 1.5 ml of methyl-t-butyl ether was added to the sample, the tube was capped and vortexed. The sample is frozen, preferably at −78° C., and the ether layer decanted into a small container, such as a second microfuge tube. The ether is evaporated to dryness under a stream of nitrogen. The residue is reconstituted in the appropriate injection solvent (125 µl of 30/70/0.1 acetonitrile/water/acetic acid) and the sample (50 µl) introduced into the liquid chromatograph/mass spectrometer. A 250 sample run can be prepared by two chemists in about 4 hours using this method.

Chromatographic separation was accomplished using a Zorbax SB-C18 50×2.1 mm (5 µm) reversed-phase HPLC column with a 0.22 µm guard frit. The column is thermostatted to 50° C. Mobile phase is 60/40/0.1 acetonitrile/water/acetic acid at a flow rate of 110 µl/min.

Analysis time is 4.5 minutes. The chromatographic eluent is split by a factor of ten and the remainder is introduced into the triple quadrupole mass spectrometer.

Here, a Perkin/Elmer API 365 triple quadrapole mass spectrometer using a Turbolonspray interface at 425° C. was utilized.

The mass spectrometer is operated in positive ion mode. Detection is by multiple reaction monitoring observing the appropriate transitions, such as the following in the case of paclitaxel:

| Paclitaxel: | 854.4 amu's to 509.2 amu's |
|---|---|
| Paclitaxel-$^{13}$C (Formula 6): | 860.4 amu's to 509.2 amu's |

Other transitions of interest include 6-alpha-hydroxy paclitaxel (870.4 to 525.2 amu's) and 3'-para-hydroxy paclitaxel (870.4 to 509.2 amu's). Settling time between each transition is adjusted to eliminate crosstalk, as known in the art.

In particular, the parent ions of paclitaxel and paclitaxel-$^{13}$C (854.4 and 860.4 amu, respectively) are selected sequentially in the first quadrupole. Each is selectively fragmented to give the diagnostic product ion of 509.2 amu in the second quadrupole, then the fragment is quantitated in the third quadrupole.

Changing the analytical process from using Taxol C to using the isotopically substituted internal standard shortened the run time and improved precision at the low levels being measured. Extraction procedures were essentially unmodified except to lower the reconstitution volume to minimize column loading time. Low flow rates coupled with a relatively high interface temperature minimized tailing of the paclitaxel peak. Use of isopropanol as an autosampler wash solvent minimized carryover.

The amount of paclitaxel in the sample can be determined in reference to the ratio of the amount of the internal standard quantitated to the known amount of the internal standard added to the sample. In particular, the amount of paclitaxel lost can be determined by dividing the amount of paclitaxel quantitated in the mass spectrometer by the above ratio. The present invention, of course, contemplates various other mathematical steps for determining the original amount of paclitaxel present in the sample based on the ratio of internal standard measured to that added, as known in the art.

The above method is easily modified to accommodate quantitation of different metabolites and paclitaxel-related compounds. Sample workup is quick and reliable, allowing throughput of approximately 250 samples per instrument per day.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A chemical compound comprising an isotopically labeled analog of a standard taxane molecule, wherein said isotopically labeled analog is synthetically formed to have incorporated therein at a selected position a stable isotope of an element existing at said selected position in said standard taxane molecule, said stable isotope having a mass different from a mass of a most abundantly occurring isotope of said element in nature, such that said isotopically labeled analog has a molecular weight different from a molecular weight of said standard taxane molecule.

2. A chemical compound according to claim 1 wherein said stable isotope is selected from the group consisting of carbon-13 and deuterium.

3. A chemical compound according to claim 1 wherein said stable isotope is incorporated at a selected position in an A-ring sidechain of said isotopically labeled analog of said standard taxane molecule.

4. A chemical compound according to claim 3 wherein said stable isotope is incorporated in a phenyl ring.

5. A chemical compound according to claim 1 wherein said isotopically labeled analog is synthetically formed to have incorporated therein a plurality of stable isotopes at a corresponding plurality of selected positions.

6. A chemical compound according to claim 5 wherein each one of said stable isotopes is an identical isotope.

7. A chemical compound according to claim 6 wherein each one of said stable isotopes is a carbon-13 isotope.

8. A chemical compound according to claim 5 wherein said molecular weight of said isotopically labeled analog significantly differs from said molecular weight of said standard taxane molecule.

9. A chemical compound according to claim 5 wherein said molecular weight of said isotopically labeled analog is distinguishable by mass spectrometry from said molecular weight of said standard taxane molecule.

10. A chemical compound according to claim 5 wherein said molecular weight of said isotopically labeled analog differs from said molecular weight of said standard taxane molecule by between about 4 and about 10 amu's.

11. A chemical compound according to claim 1 wherein said isotopically labeled analog is an isotopically labeled analog of paclitaxel.

12. A chemical compound according to claim 11 wherein said stable isotope is selected from the group consisting of carbon-13 and deuterium.

13. A chemical compound according to claim 11 wherein said isotopically labeled analog of paclitaxel is synthetically formed to have a plurality of stable isotopes incorporated therein at selected positions on an A-ring sidechain of said analog of paclitaxel.

14. A chemical compound according to claim 13 wherein a plurality of carbon atoms in the aromatic ring of the 3'-N-benzoyl group are carbon-13 atoms.

15. A chemical compound according to claim 13 wherein said molecular weight of said isotopically labeled paclitaxel analog differs from said molecular weight of a standard paclitaxel molecule by about six (6) amu's.

16. A chemical compound according to claim 1, wherein said isotopically labeled analog has a formula as follows:

wherein a majority of carbon atoms in the aromatic ring of the 3'-N-benzoyl group are carbon-13 atoms.

17. A chemical compound according to claim 1, wherein said isotopically labeled analog has a formula as follows:

wherein each carbon atom in the aromatic ring of the 3'-N-benzoyl group is a carbon-13 atom.

18. A method of producing an isotopically labeled taxane molecule, comprising the steps of:

(a) acylating a first compound having a formula as follows:

wherein $R_1$ is selected from the group consisting of $NH_2$ and $NH_3^+$, $R_2$ is selected from the group consisting of an acetyl group and a hydroxyl group, and $P_1$ is a hydroxyl protecting group or hydrogen, with an acylating agent thereby to form an intermediate compound having a C3'-N-acyl group, wherein said acylating agent is synthetically formed to have incorporated therein at a selected position a stable isotope of an element, said stable isotope having a mass different from a mass of a most abundantly occurring isotope of said element in nature; and

(b) deprotecting the intermediate compound where the intermediate compound does not already have a hydroxyl group at C2' by replacing $P_1$ with hydrogen to produce said isotopically labeled taxane molecule.

19. A method according to claim 18 wherein $R_2$ is a hydroxyl group, and including a step of selectively acylating said intermediate compound at the C-10 position prior to the step of deprotecting the intermediate compound.

20. A method according to claim 18 wherein the step of acylating the first compound is accomplished by acylating the first compound with benzoyl chloride in the presence of triethylamine, wherein a plurality of carbon atoms in the aromatic ring of the benzoyl group of the benzoyl chloride are carbon-13 atoms.

21. A method according to claim 18 wherein the first compound is formed by coupling an active ester of a protected taxane A-ring sidechain acid with a protected taxane backbone to form a coupled product, and thereafter deprotecting said coupled product to form said first compound.

22. A method according to claim 21 wherein said active ester has a formula as follows:

and wherein said protected taxane backbone is 7-CBZ baccatin III, and wherein the step of deprotecting said coupled product includes hydrogenolytic deprotection at the C-7 and 3'-N positions.

23. A method according to claim 22 wherein the hydrogenolytic deprotection at the C-7 and 3'-N positions is accomplished by adding a solution of sulfuric acid in water to a solution of said coupled product in tetrahydrofuran, followed by hydrogenation in the presence of Pearlman's catalyst.

24. A method of producing an isotopically labeled taxane molecule, comprising the steps of:

(a) condensing a (2R,3S)-2-O-benzyloxymethyl-3-N-carbobenzyloxy-3-phenylisoserine of the formula:

with N-hydroxy succinimide of the formula:

to form (2R,3S)-2-O-benzyloxymethyl-3-N-carbobenzyloxy-3-phenylisoserine N-succinimidyl active ester of the formula:

(b) esterifying said (2R,3S)-2-O-benzyloxymethyl-3-N-carbobenzyloxy-3-phenylisoserine N-succinimidyl active ester with 7-carbobenzyloxy baccatin III of the formula:

to form a N-debenzoyl-7-O,N-di(carbobenzyloxy)-2'-O-(benzyloxymethyl)paclitaxel coupled ester of the formula:

(c) deprotecting said N-debenzoyl-7-O,N-di(carbobenzyloxy)-2'-O-(benzyloxymethyl)paclitaxel coupled ester at the C-7 and 3'-N positions to form a N-debenzoyl-2'-O-(benzyloxymethyl)paclitaxel sulfate of the formula:

(d) benzoylating said N-debenzoyl-2'-O-(benzyloxymethyl)paclitaxel sulfate at the 3'-N position with benzoyl chloride in the presence of triethylamine, wherein a plurality of carbon atoms in the aromatic ring of the benzoyl group of the benzoyl chloride are carbon-13 atoms, thereby to form a 2'-O-(benzyloxymethyl) carbon-13 labeled paclitaxel of the formula:

wherein a plurality of carbon atoms in the aromatic ring of the 3'-N-benzoyl group are carbon-13 atoms; and (e) deprotecting said 2'-O-(benzyloxymethyl) carbon-13 labeled paclitaxel to form a carbon-13 labeled paclitaxel of the formula:

wherein a plurality of carbon atoms in the aromatic ring of the 3'-N-benzoyl group are carbon-13 atoms.

25. A method according to claim 24 wherein the step of benzoylating is accomplished with benzoyl chloride in the presence of triethylamine, wherein each carbon atom in the aromatic ring of the benzoyl group of the benzoyl chloride is a carbon-13 atom.

26. A method of determining the retention of a target taxane in a biological material derived from an organism that has been dosed with the target taxane, comprising the steps of:

(a) taking a selected test sample of the biological material that contains an unknown amount of the target taxane;

(b) adding a known amount of an internal standard to said test sample, wherein said internal standard is an isotopically labeled analog of the target taxane that is synthetically formed to have incorporated therein at a selected position a stable isotope of an element existing at said selected position in the target taxane, said stable isotope having a mass different from a mass of a most abundantly occurring isotope of said element in nature, such that said isotopically labeled analog has a molecular weight different from a molecular weight of the target taxane;

(c) processing said test sample to retrieve the target taxane and said internal standard from said test sample;

(d) measuring an amount of the target taxane and an amount of said internal standard retrieved from said test sample; and (e) calculating an amount of the target taxane lost during processing of said test sample based on the amount of the target taxane retrieved from said test sample and a ratio of the amount of said internal standard retrieved from said test sample to the known amount of said internal standard added to said test sample.

27. A method according to claim 26 wherein the step of taking a selected test sample includes taking a plurality of selected test samples of the biological material.

28. A method according to claim 26 wherein the step of adding includes adding an internal standard that is an isotopically labeled analog of paclitaxel.

29. A method according to claim 28 wherein said internal standard has a plurality of carbon-13 atoms in the aromatic ring of the 3'-N-benzoyl group.

30. A method according to claim 26 wherein the step of processing includes extracting the target taxane and said internal standard from said test sample by partitioning into methyl-t-butyl ether.

31. A method according to claim 30 wherein the step of processing further includes separation by liquid chromatography.

32. A method according to claim 26 wherein the step of measuring is accomplished using a mass spectrometer operated in positive ion mode.

33. A method according to claim 32 wherein the target taxane is paclitaxel, and wherein the amount of the target taxane is measured by monitoring the transition from 854.4 amu's to 509.2 amu's in said mass spectrometer.

34. A method according to claim 33 wherein said internal standard is an isotopically labeled paclitaxel molecule having a molecular weight about six (6) amu's greater than a molecular weight of the target taxane, and wherein the amount of said internal standard is measured by monitoring the transition from 860.4 amu's to 509.2 amu's in said mass spectrometer.

35. A method according to claim 26 wherein the step of calculating the amount of the target taxane lost during processing is accomplished by dividing the amount of the target taxane retrieved from said test sample by said ratio.

* * * * *